(12) United States Patent
Pertile et al.

(10) Patent No.: US 12,016,851 B2
(45) Date of Patent: Jun. 25, 2024

(54) MODIFIED RELEASE PHARMACEUTICAL FORMULATIONS COMPRISING DEFERIPRONE

(71) Applicants: Chiesi Farmaceutici S.p.A., Parma (IT); Università degli Studi di Milano, Milan (IT)

(72) Inventors: Marisa Pertile, Parma (IT); Andrea Gazzaniga, Milan (IT); Matteo Cerea, Milan (IT); Micol Cirilli, Milan (IT)

(73) Assignees: Chiesi Farmaceutici S.p.A., Parma (IT); Università degli Studi di Milano, Milan (IT)

( * ) Notice: Subject to any disclaimer, the term of this patent is extended or adjusted under 35 U.S.C. 154(b) by 0 days.

(21) Appl. No.: 17/717,922

(22) Filed: Apr. 11, 2022

(65) Prior Publication Data

US 2023/0321061 A1    Oct. 12, 2023

(51) Int. Cl.
   *A61K 31/4412* (2006.01)
   *A61K 9/20* (2006.01)

(52) U.S. Cl.
   CPC ........ *A61K 31/4412* (2013.01); *A61K 9/2009* (2013.01); *A61K 9/2013* (2013.01); *A61K 9/2036* (2013.01); *A61K 9/2054* (2013.01)

(58) Field of Classification Search
   CPC .......................... A61K 31/4412; A61K 9/2054
   See application file for complete search history.

(56) References Cited

U.S. PATENT DOCUMENTS

| | | | |
|---|---|---|---|
| 4,734,285 A * | 3/1988 | Alderman | A61K 9/2054 424/468 |
| 6,224,911 B1 * | 5/2001 | Chowhan | A61K 9/2846 424/490 |
| 7,049,328 B2 | 5/2006 | Spino et al. | |
| 8,263,125 B2 | 9/2012 | Vaya et al. | |
| 8,268,352 B2 | 9/2012 | Vaya et al. | |
| 8,563,035 B2 | 10/2013 | Cifter et al. | |
| 8,703,156 B2 | 4/2014 | Spino et al. | |
| 10,780,055 B2 | 9/2020 | Sherman et al. | |
| 10,940,115 B2 | 3/2021 | Sherman et al. | |
| 10,940,116 B2 | 3/2021 | Sherman et al. | |
| 2004/0013727 A1 * | 1/2004 | Gorissen | A61P 1/08 424/468 |
| 2006/0122273 A1 | 6/2006 | Spino et al. | |
| 2008/0085306 A1 | 4/2008 | Nangia et al. | |
| 2009/0023784 A1 | 1/2009 | Munnich et al. | |
| 2010/0255082 A1 | 10/2010 | Chauhan et al. | |
| 2011/0039911 A1 | 2/2011 | Pe'Ery | |
| 2012/0053212 A1 | 3/2012 | Shah | |
| 2012/0189692 A1 | 7/2012 | Cullen et al. | |
| 2013/0023569 A1 | 1/2013 | Spino et al. | |
| 2014/0314676 A1 | 10/2014 | Spino et al. | |
| 2014/0364491 A1 * | 12/2014 | Bortz | A61K 45/06 514/494 |
| 2018/0036228 A1 | 2/2018 | Burke et al. | |
| 2019/0117581 A1 | 4/2019 | Sherman et al. | |
| 2019/0125682 A1 | 5/2019 | Sherman et al. | |
| 2020/0188309 A1 | 6/2020 | Sherman et al. | |
| 2020/0237674 A1 | 7/2020 | Sherman et al. | |
| 2020/0253945 A1 | 8/2020 | Sherman et al. | |
| 2020/0268672 A1 | 8/2020 | Sherman et al. | |
| 2021/0386677 A1 | 12/2021 | Sherman et al. | |

FOREIGN PATENT DOCUMENTS

| | | |
|---|---|---|
| CA | 2505476 A1 | 5/2004 |
| CA | 2819234 A1 | 7/2012 |
| CN | 101352438 A | 1/2009 |
| CN | 106983746 A | 7/2017 |
| IN | 247315 | 4/1999 |
| IR | 90-07-27-71996 | 12/2011 |
| WO | WO-9718805 A1 | 5/1997 |
| WO | WO-9825905 A1 | 6/1998 |
| WO | WO-0149266 A2 | 7/2001 |
| WO | WO-0202114 A1 | 1/2002 |
| WO | WO-2004006856 A2 | 1/2004 |
| WO | WO-2006017650 A2 | 2/2006 |
| WO | WO 2008/066862 | 6/2008 |
| WO | WO-2009155088 A1 | 12/2009 |
| WO | WO-2010005851 A1 | 1/2010 |
| WO | WO-2010069920 A1 | 6/2010 |
| WO | WO-2011032000 A2 | 3/2011 |
| WO | WO-2013075015 A1 | 5/2013 |
| WO | WO-2013139931 A1 | 9/2013 |

(Continued)

OTHER PUBLICATIONS

Agrawal, S., et al., "Mitochondrial iron dysregulation in mouse and human Huntington's disease brain, Presented at Society for Neuroscience," Nov. 11-15, 2017, Washington D.C., United States, 1 page.

Agrawal, M.B, et al., "Deferiprone (KELFER), how to Make it Work More Widely, Effectively and Without Adverse Effects: An Indian Study." 1 page, 9th International Conference on Oral Chelation, Hamburg, Germany (1999).

Aguilar-De-Leyva, A., et al., "A New Deferiprone Controlled Release System Obtained by Ultrasound-assisted Compression," *Pharmaceutical Development and Technology* 19(6):728-734, Informa Healthcare, United Kingdom (Sep. 2014).

Al-Refaie, F.N., et al., "Oral Iron-chelating Therapy: the L1 Experience," *Baillière's Clinical Haematology* 7(4):941-963, Bailliere Tindall, United Kingdom (Dec. 1994).

(Continued)

*Primary Examiner* — Michael B. Pallay
(74) *Attorney, Agent, or Firm* — Sterne Kessler Goldstein & Fox P.L.L.C.

(57) ABSTRACT

The disclosure is directed to pharmaceutical compositions for oral administration in form of coated tablets that exhibit modified release properties when administered as either whole or half tablets. In particular, the disclosure is directed to modified release tablets comprising deferiprone, said tablets being suitable for twice daily oral administration. The disclosure is also directed to methods of making and using the same.

18 Claims, 6 Drawing Sheets

(56) References Cited

FOREIGN PATENT DOCUMENTS

| WO | WO-2014072673 A1 | 5/2014 |
|---|---|---|
| WO | WO-2015087258 A1 | 6/2015 |
| WO | WO 2019/082128 | 5/2019 |

OTHER PUBLICATIONS

Anderson, L.J., et al., "Comparison of Effects of Oral Deferiprone and Subcutaneous Desferrioxamine on Myocardial Iron Concentrations and Ventricular Function in Beta-thalassaemia," *Lancet* 360: 516-520, Elsevier, United Kingdom (Aug. 2002).

Azarkeivan, A., et al., "Evaluation of gastric side effects of new form of Deferiprone, (L1; Enteric coated) in Thalassemia major patients," *Sci J Iran Blood Transfus Organ* 13(3): 163-169, Iranian Blood Transfusion Organization Research Center, Iran (2016).

Cabantchik, Z.I., et al., "Regional siderosis: a new challenge for iron chelation therapy," *Frontiers in Pharmacology* 4(167): 1-7, Frontiers, Switzerland (2013).

Chen, J., et al., "Iron Accumulates in Huntington's Disease Neurons: Protection by Deferoxamine," *PLOS one* 8(10):e77023, pp. 1-12, Public Library of Science, United States (2013).

Clinical Trials. Retrieved from the Internet: (URL: https://clinicaltrials.gov/ct2/results?term=deferiprone&no_unk=Y). (retrieved on Nov. 15, 2018.).

Cossu, G., et al., "Efficacy and safety of deferiprone for the treatment of pantothenate kinase-associated neurodegeneration (PKAN) and neurodegeneration with brain iron accumulation (NBIA): results from a four years follow-up," *Parkinsonism & Related Disorders* 20(6):651-654, Elsevier, Netherlands (2014).

Crosland, R.D., et al., "Action of Reactive Oxygen Species and Their Antagonists on Twitch Tension of the Rat Phrenic Nerve-diaphragm," *Pharmacology & Toxicology* 77(3):231-237, Nordic Pharmacological Society : Distributed by Blackwell Munksgaard, Denmark (Sep. 1995).

Eleftheriou A., "about thalassemia," thalassemia international federation, pp. 1-178 (2003).

Galanello, R., "Deferiprone in the treatment of transfusion-dependent thalassemia: a review and perspective," *Ther Clin Risk Manag.* 3(5):795-805, Dovepress, United Kingdom (2007).

Grady, R.W and Giardina, P.J., "Iron Chelation: Rationale for Combination Therapy," *Iron Chelators: New Development Strategies*, pp. 293-310 Ponte Vedra Beach, FL: Saratoga group (2000).

Grady, R.W., et al., "Iron Chelation: Combined Therapy May Be a Better Approach." 1 page, 9$^{th}$ International Conference on Oral Chelation, Hamburg, Germany (1999).

Grubman, A., et al., "Mitochondrial Metals as a Potential Therapeutic Target in Neurodegeneration," *British Journal of Pharmacology* 171(8): 2159-2173, Wiley, United Kingdom (Apr. 2014).

Hatcher, H.C., et al., "Synthetic and Natural Iron Chelators: Therapeutic Potential and Clinical Use," *Future Medicinal Chemistry* 1(9), pp. 1-35 Future Science, United Kingdom (Dec. 2009).

Heli, H., et al., "Advances in Iron Chelation: an Update," *Expert Opinion on Therapeutic Patents* 21(6): 819-856, Informa Healthcare, United Kingdom (Jun. 2011).

Hoffbrand, A.V, "Oral Iron Chelation," *Seminars in Hematology* 33(1): 1-8, W.B. Saunders, United States (Jan. 1996).

Kakhlon, O., et al., "Iron Redistribution as a therapeutic strategy for treating diseases of localized iron accumulation," *Canadian Journal of Physiology and Pharmacology* 88(3):187-196, NRC Research Press, Canada (2010).

Kaul, D. and Taram, S.V., "Dual Control over release of a water soluble drug from compressed tablets," *Indian Journal of Pharmaceutical Sciences* 56(1);15-18, The Indian Pharmaceutical Society, India (1994).

Kaul, D. and Venkataram, S., "Sustained Release Tablet Formulation for a new Iron Chelator," *Drug Development and Industrial Pharmacy* 18(9):1023-1035, Taylor & Francis, United Kingdom (1992).

Kaul, D., et al., "Crystal Habit modifications and altered tableting characteristics," *International Journal of Pharmaceutics* 88(1-3):345-350, Elsevier, Netherlands (1992).

Kontoghiorghes, G.J., et al., "Safety Issues of Iron Chelation Therapy in Patients With Normal Range Iron Stores Including Thalassaemia, Neurodegenerative, Renal and Infectious Diseases," *Expert Opinion on Drug Safety* 9(2):201-216, Taylor & Francis, United Kingdom (Mar. 2010).

Kontoghiorghes, G.J., et al., "Benefits and Risks of Deferiprone in Iron Overload in Thalassaemia and Other Conditions: Comparison of Epidemiological and Therapeutic Aspects With Deferoxamine," *Drug Safety* 26(8):553-584, Springer International, New Zealand (2003).

Kontoghiorghes, G.J., et al., "Risk/benefit Assessment, Advantages Over Other Drugs and Targeting Methods in the Use of Deferiprone as a Pharmaceutical Antioxidant in Iron Loading and Non Iron Loading Conditions," *Hemoglobin* 33(5):386-397, Informa Healthcare, United Kingdom (2009).

Kontoghiorghes, G.J., et al., "The Role of Iron and Chelators on Infections in Iron Overload and Non Iron Loaded Conditions: Prospects for the Design of New Antimicrobial Therapies," *Hemoglobin* 34(3):227-239, Informa Healthcare, United Kingdom (Jun. 2010).

Kwiatkowski, A., et al., "Long-term Improvement Under Deferiprone in a Case of Neurodegeneration With Brain Iron Accumulation," *Parkinsonism and Related Disorders* 18(1):110-112, Elsevier Science, United Kingdom (Jan. 2012).

NCT02465489, Trial No. LA51-0115, "Single-dose pharmacokinetic study of deferiprone extended release tablets versus Ferriprox immediate release tablets under fasting and fed condition in healthy volunteers," ClinicalTrials.gov, Phase 1, accessed at URL:[https://clinicaltrials.gov/ct2/show/NCT02465489?term=LA51-0115&draw=1&rank=1] on Jul. 20, 2020, 18 pages.

Levy, M., et al., "Pilot safety trial of deferiprone in 10 subjects with superficial siderosis," *Stroke* 43(1): 120-124, Lippincott Williams & Wilkins, United States (2012).

Moreau, C., et al., "Could conservative iron chelation lead to neuroprotection amyotrophic lateral sclerosis?," *Antioxid Redox* 29(8), 17 pages Mary Ann Liebert, United States (2018).

Morel, I., et al., "Antioxidant and Free Radical Scavenging Activities of the Iron Chelators Pyoverdin and Hydroxypyrid-4-ones in Iron-loaded Hepatocyte Cultures: Comparison of Their Mechanism of Protection With That of Desferrioxamine," *Free Radical Biology and Medicine* 13(5):499-508, Elsevier Science, United States (Nov. 1992).

NCT02442310, Comparison of Deferiprone Delayed Release tablets and Deferiprone Oral Solution in Healthy Volunteers, ClinicalTrials.gov, published May 13, 2016, accessed at https://clinicaltrials.gov/ct2/show/NCT02442310, accessed on May 25, 2017, 4 pages.

Peng, C-T., et al., "Safety Monitoring of Cardiac and Hepatic Systems in Beta-thalassemia Patients With Chelating Treatment in Taiwan," *European Journal of Haematology* 70(6):392-397, Blackwell, United Kingdom (Jun. 2003).

Pennell, D.J., et al., "Randomized Controlled Trial of Deferiprone or Deferoxamine in Beta-thalassemia Major Patients With Asymptomatic Myocardial Siderosis," *Blood* 107(9):3738-3744, American Society of Hematology, United States (May 2006).

Reeder, B.J., et al., "Tyrosine as a Redox-active Center in Electron Transfer to Ferryl Heme in Globins," *Free Radical Biology and Medicine* 44(3):274-283, Elsevier Science, United States (Feb. 2008).

Sheth, S., "Iron Chelation: an update." *Curr Opin Hematol* 21(0), pp. 1-7 Wolters Kluwer, Netherlands (2014).

Song, D., et al., "Systemic administration of the iron chelator deferiprone protects against light-induced photoreceptor degeneration in the mouse retina," *Free Radical Biology and Medicine* 53(1):64-71, Elsevier, Netherlands (2012).

Spiegel, B.M., et al., "Understanding gastrointestinal distress: a framework for clinical practice," *Am J Gastroenterol* 106(3):380-385, Nature Publishing Group, United States (2011).

Stumpf, J.L, "Deferasirox," *American Journal of Health-System Pharmacy* 64(6):606-616, American Society of Health-System Pharmacists, United States (Mar. 2007).

(56) References Cited

OTHER PUBLICATIONS

Thalassemia therapy, Deferasirox and Deferiprone are useful for iron overload in thalassemia major, Medical letter on the CDC & FDA; 88, 3 pages (2006).

Thompson, M.G., et al., "Antibacterial Activities of Iron Chelators Against Common Nosocomial Pathogens," *Antimicrobial Agents and Chemotherapy* 56(10):5419-5421, American Society for Microbiology, United States (Oct. 2012).

Transfusion medicine, Deferiprone shows potential for first-line iron chelation drug obesity, fitness & wellness week; 1498, 3 pages (2005).

Tsou, A.Y., et al., "Pharmacotherapy for Friedreich Ataxia," *CNS Drugs* 23(3):213-223, Springer International, New Zealand (2009).

Venkataram, S and Khohlokwane, M, "Microencapsulation of an Iron Chelator for Sustained Release and Crystal Habit Modification," *Journal of Microencapsulation* 13(5):519-525, Informa Healthcare, United Kingdom (Sep.-Oct. 1996).

Waldmeier, P.C., et al., "Inhibition of Catechol-o-methyltransferase (Comt) as Well as Tyrosine and Tryptophan Hydroxylase by the Orally Active Iron Chelator, 1,2-dimethyl-3-hydroxypyridin-4-one (L1, Cp20), in Rat Brain in Vivo," *Biochemical Pharmacology* 45(12):2417-2424, Elsevier Science, United Kingdom (Jun. 1993).

Ware, H.M. and Kwiatkowski, J.L., "Evaluation and Treatment of Transfusional Iron Overload in Children," *Pediatr Clin N Am* 60:1393-1406, Elsevier, Netherlands (2013).

Weigel, K.J., et al., "Iron chelation and multiple sclerosis," *ASN Neuro* 6(1): 44-63, Sage Publications, United States (2014).

Whiteside, D.P., et al., "Pharmacokinetic Disposition of the Oral Iron Chelator Deferiprone in the Domestic Pigeon (*Columba livia*)," *Journal of Avian Medicine and Surgery* 21(2):121-129, Association of Avian Veterinarians, United States (Jun. 2007).

NCT02728843, "Study of Parkinson's Early Stage with Deferiprone (SKY)", ClinicalTrials.gov, accessed at https://clinicaltrials.gov/ct2/show/NCT02728843?term=02728843&rank=1, accessed on Jan. 4, 2019, 7 pages.

Hoffbrand, A.V., et al., "Role of Deferiprone in chelation therapy for transfusional iron overload," *Blood* 102(1):17-24, American Society of Hematology, United States (2003).

Morales, N.P., et al., "Bioequivalence study of a film-coated tablet of deferiprone in healthy Thai volunteers," *International Journal of Clinical Pharmacology and Therapeutics* 47(5):358-364, American Society of Pharmacology & Therapeutics, United States (2009).

Rujivipat, S., and Bodmeier, R., "Improved Drug delivery to the lower intestinal tract with tablets compression-coated with enteric/nonenteric polymer powder blends," *European Journal of Pharmaceutics and Biopharmaceutics* 76:486-492, Elsevier, Netherlands (2010).

"Clinical Trial: Comparison of Deferiprone Delayed Release Tablets and Deferiprone Oral Solution in Healthy Volunteers." Indian eGov Newswire, May 26, 2015.Infotrac Newsstand, http://link.galegroup.com/apps/doc/A414977911/STND?u-tplmain&sid=STND&xid=e7ec89ba.

Clinical Trials, "Comparison of Deferiprone Delayed Release Tablets and Deferiprone Oral Solution in Healthy Volunteers," available at, https://clinicaltrials.gov/ct2/history/NCT02442310?V_4=View#StudyPageTop, (last accessed on Jan. 30, 2020), Published May 13, 2016, pp. 1-25.

Felton, L. (Ed.), "Remington: Essentials of Pharmaceutics," Chapters 2, 30-32 and Appendix B., Pharmaceutical Press, London, UK, (2013).

Hilton, A., et al., "Use of Hydoxypropyl Methylcellulose Acetate Succinate in an Enteric Polymer Matrix To Design Controlled-Release Tablets of Amoxicillin Trihydrate," *Journal of Pharmaceutical Sciences*, 82(7): 737-743, American Pharmaceutical Association, United States (1993).

FERRIPROX® (deferiprone) tablets, for oral use, prescribing information, Oct. 2011, accessed at URL:[https://www.accessdata.fda.gov/drugsatfda_docs/label/2011/021825lbl.pdf] on Jul. 19, 2019, 7 pages.

Co-pending Application, U.S. Appl. No. 17/717,922, inventors Pertile, Marisa, et al., filed Apr. 11, 2022.

Aburahma, M. H., and Badr-Eldin, S. M., "Compritol 888 ATO: a multifunctional lipid excipient in drug delivery systems and nanopharmaceuticals," Expert Opin Drug Deliv 11(12):1865-1883, Taylor & Francis, United Kingdom (2014).

Campos-Aldrete, M. A., et al., "Influence of the viscosity grade and the particle size of HPMC on metronidazole release from matrix tablets," European Journal of Pharmaceutics and Biopharmaceutics 43(2):173-178, Elsevier, Netherlands (1997).

Cao, Q.-R., et al., "A formulation approach for development of HPMC-based sustained release tablets for tolterodine tartrate with a low release variation," Drug Development and Industrial Pharmacy 39(11):1720-1730, Informa Healthcare, United States (2013).

El-Halim, S. M. A., et al., "Comparative study on the different techniques for the preparation of sustained-release hydrophobic matrices of a highly water-soluble drug," Drug Discov Ther 4(6):484-492, International Advancement Center for Medicine & Health Research Co., Ltd., Japan (2010).

Li, F.-Q., et al., "In vitro controlled release of sodium ferulate from Compritol 888 ATO-based matrix tablets," Int J Pharm 324(2):152-157, Elsevier, Netherlands (2006).

Roberts, M., et al., "Development and evaluation of sustained-release Compritol® 888 ATO matrix mini-tablets," Drug Dev Ind Pharm 38(9):1068-1076, Informa Pharmaceutical Science, United Kingdom (2012).

Roberts, M., et al., "Preparation and characterization of Compritol 888 ATO matrix tablets for the sustained release of diclofenac sodium," Pharmaceutical Development and Technology 20(4):507-512 (early online 1-6), Taylor & Francis, United Kingdom (published online Dec. 2013; published in print Jun. 2015).

Rosiaux, Y., et al., "Optimizing a wet granulation process to obtain high-dose sustained-release tablets with Compritol 888 ATO," Drug Dev Ind Pharm 41(10):1738-1744, Informa Pharmaceutical Science, United Kingdom (2015).

Vazquez, M.-J., et al., "Atenolol release from hydrophilic matrix tablets with hydroxypropylmethylcellulose (HPMC) mixtures as gelling agent: effects of the viscosity of the HPMC mixture," European Journal of Pharmaceutical Science 4(1):39-48, Elsevier, Netherlands (1996).

Cohen, E.R., et al., "Safety profile of the oral iron chelator deferiprone: a multicenter study," *Br J Haematology* 108:305-312, Blackwell Science Ltd., United States (2000).

European Pharmacopoeia 4$^{th}$ Ed., Supplement 4.3, p. 2891, Directorate for the quality of Medicines of the Council of Europe, France (2003).

Galanello, R., et al. "A prospective randomized controlled trial on the safety and efficacy of alternating deferoxamine and deferiprone in the treatment of iron overload in patients with thalassemia," *Haematologica* 91(9):1241-1243, Ferrata Storti Foundation, Italy (2006).

Hider, R.C. and Hoffbrand, A.V., "The Role of Deferiprone in Irone Chelation," *N Engl J Med*. 379:2140-2150, Massachusetts Medical Society, United States (2018).

Maggio, A., et al., "Deferiprone versus deferoxamine in patients with thalassemia major: a randomized clinical trial," Blood Cells Mol Dis. 28(2):196-208, Elsevier, Netherlands (2002).

Beeckmans, D., et al., "Altered duodenal bile salt concentration and receptor expression in functional dyspepsia," United European Gastroenterol J 6(9):1347-1355, John Wiley & Sons, United States (Nov. 2018).

Dahlgren, D., et al., "Fasted and fed state human duodenal fluids: Characterization, drug solubility, and comparison to simulated fluids and with human bioavailability," Eur J Pharm Biopharm 163:240-251, Elsevier, Netherlands (Jun. 2021).

* cited by examiner

MODIFIED RELEASE PHARMACEUTICAL FORMULATIONS COMPRISING DEFERIPRONE

FIELD OF THE DISCLOSURE

The disclosure relates to pharmaceutical formulations comprising the iron chelator deferiprone. In particular, the disclosure is directed to modified release formulation suitable for twice-a-day oral administration for the treatment of patients suffering from for example, thalassemia, sickle cell anemia, hemochromatosis, and myelodysplasia.

BACKGROUND OF THE DISCLOSURE

Deferiprone, also known as 3-hydroxy-1,2-dimethylpyridin-4-one, is a bidentate ligand which binds to iron in a 3:1 molar ratio.

It is used in the treatment of generalized iron overload, particularly in conditions where frequent blood transfusions lead to iron overload including, e.g., thalassemia and Sickle Cell Disease.

The introduction of deferiprone in the current therapy has represented an important advancement as it Liver Iron Concentration (LIC) and cardiac iron overload. In particular, Maggio A, et al., Blood Cells Mol Dis. 2002, 28(2):196-208 and Galanello R, et al., Haematologica. 2006, 91(9):1241-1243 suggested that deferiprone monotherapy seems to be superior to deferoxamine monotherapy in improving myocardial siderosis and cardiac function.

With regard to safety, the most frequent adverse events are gastrointestinal disorders due to gastrointestinal irritation. Such discomfort could cause patients to refrain from taking the medication, leading to a worsening of their condition. Other observed adverse events are musculoskeletal disorders (arthralgia), Alanine Aminotransferase (ALT) increase, agranulocytosis and neutropenia.

Agranulocytosis seems to be an idiosyncratic response and it is more frequent in the first year of treatment. The incidence of neutropenia and agranulocytosis is stable and seems to be not related with dose (Hider R C et al N Engl J Med. 2018; 379:2140-2150).

Deferiprone is endowed with a long half-life of 2-3 hour) and an unpleasant bitter taste too.

Said drug is sold as Immediate Release (IR) 500 mg and 1000 mg tablets, as well as a 100 mg/ml liquid formulation, generally, under the trade name Ferriprox®.

In view of its pharmacological and ADME profile, and in order to improve the compliances of the patients, recently, deferiprone has also been launched commercially as 1000 mg Delayed Release (DR) tablets for oral administration.

The composition of the DR tablets has been disclosed in WO 2019/082128, and it comprises: (a) a core comprising the active pharmaceutical ingredient and an enteric polymer with pH-dependent solubility, and (b) an enteric coating.

In fact, the oral pharmaceutical dosage forms containing deferiprone, due to its potential for irritation and damage to the gastric mucosa and the relatively high solubility in an acid environment, has to be provided with an enteric coating (e.g. polymeric films with solubility at pH>5) in order to avoid, or at least reduce, the release of the active principle during the permanence of the unit in the stomach, avoiding reaching plasma concentrations responsible for possible systemic adverse reactions.

To sustain the release, in the case of the marketed deferiprone product, an enteric polymer with pH-dependent solubility, hydroxypropyl methylcellulose acetate succinate (HPMC-AS) in the tablet core is used.

Said tablets are suitable for a twice daily administration being bioequivalent in the steady state to the same daily dose of an immediate release tablet administered three times daily.

The commercial tablets are also debossed with a score line, to make it easy for the patient to break the tablets into two approximately equal parts for dosing flexibility.

To sustain the release, in the case of the marketed deferiprone product, an enteric polymer in the tablet core, hydroxypropyl methylcellulose acetate succinate (HPMC-AS) is used.

However, HPMC-AS has a pH-dependent solubility.

This could lead to a release influenced by the external environment that the formulation has to face during the transit along the regions in which the release of the active agent takes place, which are characterized by physiological fluids having different pHs. Hence, the release can be less predictable being at the mercy of random microenvironmental variation of the pH.

Therefore, it would be advantageous to provide a tablet suitable for twice a day oral administration, with improved properties in terms of reproducibility of the expected release profiles.

The technical solution is provided by various aspects of the present disclosure.

SUMMARY

In one aspect is provided a modified release tablet comprising: (a) a core comprising deferiprone in an amount of about 85.0% to about 95.0% by weight of the tablet, a modifying release agent comprising a hydroxypropylmethylcellulose polymer having a viscosity of 100 cP and optionally a hydroxypropylmethylcellulose polymer having a viscosity of 4000 cP in an amount of about 5.0% to about 10.0% by weight of the tablet, a lubricant and/or glidant in an amount of about 0.2% to about 2.0% by weight of the tablet, and additional pharmaceutically acceptable excipients in an amount of about 0.0 to 5.0% by weight of the tablet; and (b) an enteric coating; wherein the tablet is suitable for twice a day oral administration.

In another aspect is provided a pharmaceutical formulation in form of modified release enteric coated tablets suitable for twice-a-day oral administration, wherein the pharmaceutical formulation is a tablet, and wherein the core of the tablet comprises deferiprone in an amount of about 85.0 to 95.0%, a hydroproylmethylcellulose polymer having a viscosity of 100 cP alone or in mixture thereof with a hydroproylmethylcellulose polymer having a viscosity of 4000 cP as a modifying release agent in an amount of about 5.0 and 10.0%, a lubricant and/or glidant in an amount of about 0.2 to 2.0%, and other suitable pharmaceutically acceptable excipients in an amount of about 0 to 5%, wherein all the amounts calculated by weight on the total weight of the formulation.

In some aspects, the modifying release agent comprises a hydroxypropylmethylcellulose polymer having a viscosity of 100 cP in an amount of about 7.5% by weight. In some aspects, the modifying release agent comprises a mixture of hydroxypropylmethylcellulose polymer having a viscosity of 100 cP and a hydroxypropylmethylcellulose polymer having a viscosity of 4000 cP in an amount of about 5% by weight. In some aspects, the ratio between the hydroxypropylmethylcellulose polymer having a viscosity of 100 cP and the hydroxypropylmethylcellulose polymer having a viscosity of 4000 cP is 40:60.

In some aspects, the lubricant is selected is selected from the group consisting of magnesium stearate, calcium stearate, stearic acid, sodium stearyl fumarate, talc, and combinations thereof. In some aspects, the lubricant is magnesium stearate.

In some aspects, the glidant is selected from the group consisting of colloidal silicon dioxide, starch, talc, and combinations thereof. In some aspects, the glidant is colloidal silicon dioxide.

In some aspects, the other suitable pharmaceutically acceptable excipients are selected from pH adjusting agents and bulking agents.

In some aspects, the enteric coating comprises an enteric polymer, a diluent, and optionally a plasticizer. In some aspects, the enteric coating comprises an ethacrylic acid—ethyl acrylate copolymer (1:1) dispersion in water and propylene glycol. In some aspects, the enteric coating comprises methacrylic acid—methacrylate copolymer (1:1) in an alcoholic solution with triethyl citrate.

In some aspects, the core of the tablet comprises from 500 to 1500 mg of deferiprone. In some aspects, the core of the tablet comprises 1000 mg of deferiprone.

In another aspect is provided a process for the preparation of the modified release tablet as described herein, said process comprising:
 (i) mixing deferiprone with the modifying release agent and the additional pharmaceutically acceptable excipients, if present to form a mixture;
 (ii) wet-granulating the mixture obtained in step (i) in a high shear granulator followed by drying and screening to produce a granulate;
 (iii) mixing the granulate obtained in step (ii) with the lubricant/glidant to form a mixture;
 (iv) compressing the mixture obtained in step (iii) to form a tablet; and
 (v) coating the tablet.

In another aspect is provided a process for the preparation of the modified release tablet as described herein, said process comprising:
 (i) mixing deferiprone with the modifying release agent and the additional pharmaceutically acceptable excipients, if present;
 (ii) adding the lubricant/glidant and further mixing to form a mixture;
 (iii) directly compressing the mixture obtained in step (ii) to form a tablet; and
 (iv) coating the tablet.

In another aspect is provided the modified release tablet as described herein for use in the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

In another aspect is provided a method of treating a disease which causes an overload of iron, comprising administering the modified release tablet as described herein. In some aspects, the disease is thalassemia or sickle cell anemia. In some aspects, the iron overload is transfusional iron overload.

In another aspect is provided a method of treating and/or preventing a disease which is caused by an overload of iron, comprising administering the modified release tablet as described herein. In some aspects, the iron overload is transfusional iron overload.

In another aspect is provided the modified release tablet as described herein for the manufacture of a medicament for the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload. In another aspect is provided a method for the treatment of diseases which cause an overload of iron, or for the prevention and/or treatment of diseases which are caused by an overload of iron in a patient in a need thereof, said method comprising orally administering the disclosed pharmaceutical composition.

DEFINITIONS

Figure 1:
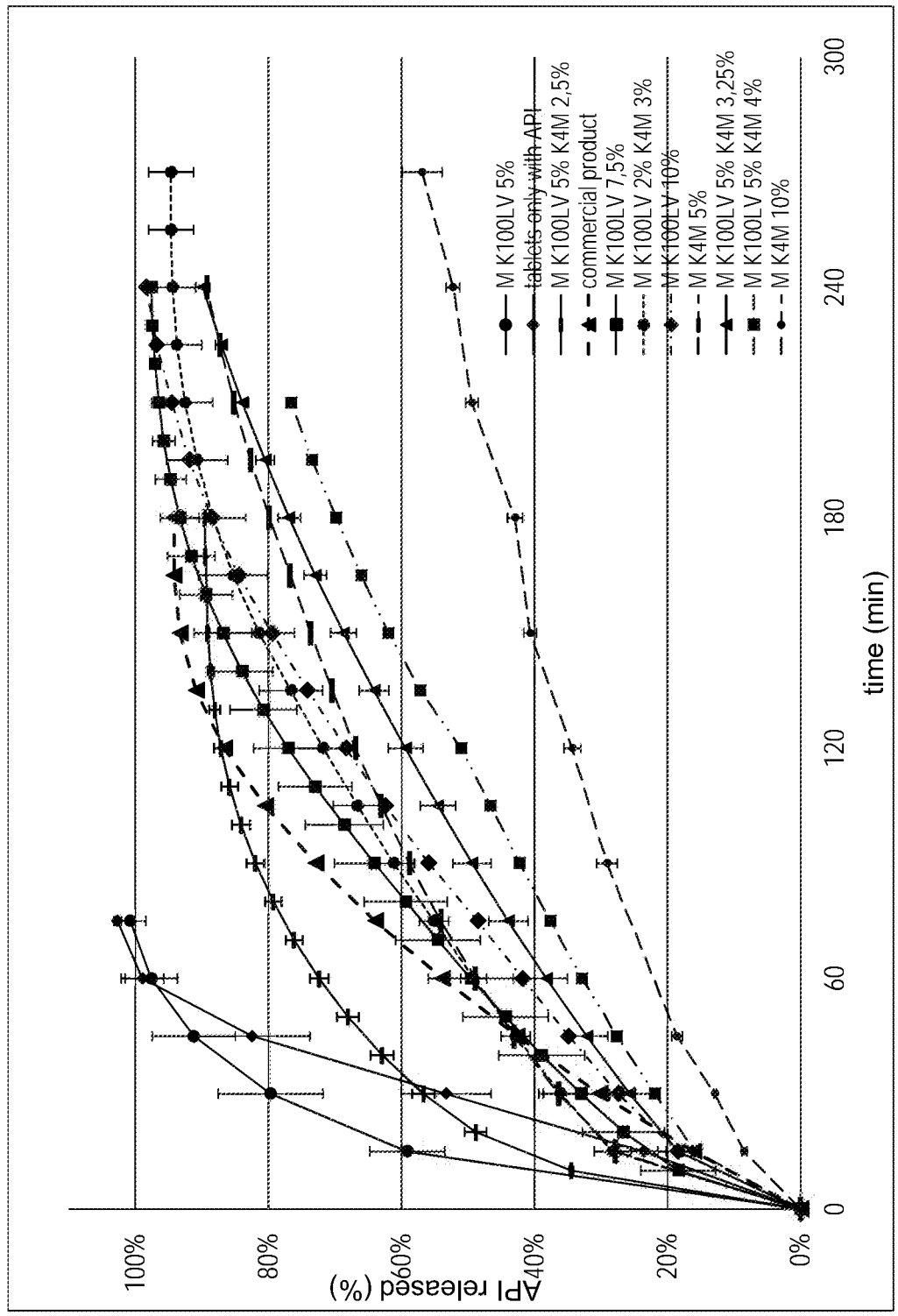
FIG. 1: Dissolution tests of HPMC formulations carried out in 900 ml of pH 6.8 medium, basket (apparatus 1) having rotational speed of 100 rpm. The line with a triangular indicator is referred to as the commercial product.

As used herein, the indefinite articles "a" or "an" should be understood to refer to "one or more" of any recited or enumerated component. For example, "a tablet" refers to one or more tablets.

Also as used herein, "and/or" refers to and encompasses any and all possible combinations of one or more of the associated listed items, as well as the lack of combinations when interpreted in the alternative ("or").

When the term "about" is used in conjunction with a numerical value or range, it modifies that value or range by extending the boundaries above and below the numerical values set forth. The term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.).

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed is also disclosed. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

The terms "iron overload" or "overload of iron" are used interchangeably herein and refer to medical conditions where the body contains or stores too much (or "excess") iron. An example is transfusional iron overload, where the excess iron is introduced by one or more blood transfusions.

Wherever aspects are described herein with the language "comprising," otherwise analogous aspects described in terms of "consisting of and/or" consisting essentially of are also provided. To the extent that the term "includes" or "including" is used in the specification or the claims, it is intended to be inclusive in a manner similar to the term "comprising" as that term is interpreted when employed as a transitional word in a claim.

As used herein, the term "active ingredient" or "active pharmaceutical ingredient" (API) or "drug" are used as synonymous and mean any component that is intended to furnish pharmacological activity or other direct effect in the diagnosis, cure, mitigation, treatment, or prevention of disease, or to affect the structure or any function of the body of man or other animals.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

Conversely, the term "hydrophobic" denotes a compound tending to be electrically neutral and non-polar, and thus preferring other neutral and nonpolar solvents or molecular environments.

For "pH dependent solubility" it is meant a substance having different solubilities at different pHs. These pH-dependent solubility differences lead to pH-dependent dissolution profiles.

The expression "insoluble or poorly water soluble" refers to a substance having a solubility in water as defined in the European Pharmacopoeia Ed. 4$^{th}$, 2003, page 2891.

"Core" or "tablet core" as used herein comprises an active ingredient, e.g., deferiprone, and one or more excipients compressed into an uncoated tablet. The core can be coated with various coatings, including an enteric coating.

In the present context, the terms "controlled release", "prolonged release", "modified release" and "delayed release" are intended to be equivalent terms covering any type of release of deferiprone from a composition of the disclosure that is appropriate to obtain a specific therapeutic or prophylactic response after administration to a subject". The terms refer to protecting an active ingredient, e.g., deferiprone, from rapid release at acidic pH, e.g., in the stomach, while enabling the active ingredient to be released at a higher rate at a higher pH, e.g., in the intestines. In some aspects, DR will be understood to mean that, when tested in USP apparatus 2 at 75 rpm, the extent of dissolution will be around 20±5% at 1 hour in 0.1N HCl, and the rate of dissolution will be substantially higher (e.g., over 30%, e.g. over 40%, in 1 hour) in phosphate buffer with pH 6.8 than the rate of dissolution in 0.1N HCl.

"Disintegrant" as used herein refers to an excipient that is insoluble in water, but swells when wetted to cause a tablet to disintegrate.

"Dissolution" as used herein refers to the process by which a solute forms a solution in a solvent.

"Enteric coat" or "enteric coating" as used herein refers to a coating comprising an enteric polymer. An enteric coating can serve to prevent or delay a tablet's dissolution or disintegration in a gastric environment.

For "burst effect" it is meant the initial rapid release before the release rate reaches a stable profile, occurring immediately upon at the change of pH in the release medium.

"Enteric coated tablet" means a tablet having a core comprising an active ingredient, which is coated with an enteric coating.

"Enteric polymer" as used herein is understood to mean a polymer that is relatively insoluble at the acidic pH of the fasted stomach (e.g., about pH 1 to about pH 4), but soluble at higher pH (e.g., about pH 4.5 to about pH 8), which corresponds to the pH in the small intestine or thereafter, particularly in the duodenum or ileum.

The terms "fillers", "diluents" and "bulking agents" are used as synonymous.

With the term "bioequivalence" it is meant the absence of a significant difference between the bioavailability, i.e., the extent of absorption and peak concentration, between two pharmaceutical drug products (e.g., a test product and a reference product) over the course of a period of time, at the same dose and under the same conditions, The determination of whether or not a test product is bioequivalent to a reference product is determined by performing a study, referred to as a bioequivalence or comparative bioavailability study, in a group of subjects, usually about 18-36 subjects or more, under controlled conditions.

The study can be done in a "crossover" design, which means that the study is done in 2 or more phases, usually at least a week apart, depending in part on the half-life of the drug. In the first phase, half the subjects are randomly assigned to ingest the test product first and the other half ingest the reference product first. In the second phase, each subject ingests the alternate product.

In each phase, blood samples are drawn from each subject, on a predetermined schedule after ingestion of the test product. The blood samples are then analyzed to determine serum concentrations of the drug (test product, e.g., deferiprone) at each time point. For example, drugs are bioequivalent if they enter circulation at the same rate when given in similar doses under similar conditions. Parameters often used in bioequivalence studies are $t_{max}$, $C_{max}$, $C_{min}$, $AUC_{0\text{-}infinity}$, $AUC_{0\text{-}t}$.

In the present context "$t_{max}$" denotes the time to reach the maximal plasma concentration ($C_{max}$) after administration; $AUC_{0\text{-}infinity}$ denotes the area under the plasma concentration versus time curve from time 0 to infinity; $AUC_{0\text{-}t}$ denotes the area under the plasma concentration versus time curve from time 0 to time t; W50 denotes the time where the plasma concentration is 50% or more of $C_{max}$; W75 denotes the time where the plasma concentration is 75% or more of $C_{max}$; and MRT denotes mean residence time for tacrolimus.

"Fasted state" as used herein refers to abstinence from food for a defined period of time after a meal (typically, at least several hours, e.g., 4 or 6 hours, after a meal).

"Fed state" as used herein refers to administration with a meal or soon after a meal (e.g., within about 1 hour).

The term "chemical stable" refers to stability of the active agent in the formulation, wherein changes in the drug assay values and/or impurities content are equal to or lesser than 5%, preferably lesser than 3%, during storage at 25° C. and 60% relative humidity (RH), or 40° C. and 75% RH, for at least 1 month.

The term "vitro-in vivo correlation (IVIVC)" refers an in vitro dissolution test that is predictive of the in vivo performance of the drug product.

"Gastric distress" as used herein refers to discomfort of the gastrointestinal (GI) tract, e.g., one or more of pain, cramping, bloating, nausea, indigestion, heartburn, and gas.

"Half tablet" as used herein means either of the two parts of a tablet obtained by splitting the tablet into two parts of equal or approximately equal weight. In some aspects, a half tablet is from about 40% to about 60% by weight of the whole tablet from which the half was derived. In some aspects, the approximately equal weight of each half tablet is about 45-55% of the total weight of the whole tablet.

"Percent" or "%" as used herein refers to weight percentage (w/w) unless otherwise specified.

"Scored tablet" as used herein refers to a tablet that is debossed with one or more lines, also known as a "score line", to facilitate splitting the tablet, e.g., to enable administration of a half tablet. In some aspects, the tablet can be scored with two, three, four, or more score lines.

"Tablet" as used herein refers a solid oral pharmaceutical dosage form. In some aspects, the tablet is a compressed tablet.

"Whole tablet" means a complete tablet, i.e., not broken or split into parts.

In the present context, viscosity is expressed in centipoise (1 cP=0.01 P) which is more commonly used than the poise itself. The analogous unit in the International System of Units is the pascal-second (Pa-s). 1 cP corresponds to 1 mPa s.

Terms such as "treating" or "treatment" or "to treat" or "ameliorating" or "alleviating" or "to alleviate" can refer to both 1) therapeutic measures that cure, slow down, lessen symptoms of, reverse, and/or halt progression of a diagnosed pathologic condition or disorder and 2) prophylactic or preventative measures that prevent, reduce the incidence of, reduce the risk of, and/or slow the development of a targeted pathologic condition or disorder. Thus, those in need of treatment include those who already have the disorder; those prone to developing the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those who already have the condition or disorder as well as those prone to developing the condition or disorder or those in which the condition or disorder is to be prevented or incidence reduced.

By "subject" or "individual" or "patient," is meant any human subject, for whom diagnosis, prognosis, treatment, or therapy is desired.

By "therapeutically effective dose or amount" or "effective amount" is intended an amount of active pharmaceutical ingredient, e.g., deferiprone, that when administered brings about a positive therapeutic response with respect to treatment of or reducing the risk of a disease in a subject to be treated.

It will be understood that the deferiprone DR tablets used as the "reference" or "reference product" herein are Ferriprox® tablets (1000 mg) as approved by FDA and sold in the United States.

DETAILED DESCRIPTION

The present disclosure provides pharmaceutical formulations for the prevention and/or treatment of diseases which are caused by an overload of iron, especially compositions providing modified release of the active ingredient. In some aspects, the pharmaceutical formulations are tablets. In some aspects, the pharmaceutical formulations are modified release tablets.

The active ingredient in the disclosed pharmaceutical formulations is deferiprone. However, within the scope of the present disclosure is deferiprone in any physical form (crystals, amorphous powder, any possible polymorphs, any possible solvate). Included are also pharmaceutically acceptable salts and/or solvates thereof. In some aspects, deferiprone is used as a base in its anhydrous form.

It has been found that the disclosed pharmaceutical formulations with hydrophilic polymers as modifying release agents exhibit an in vitro release profile similar to the commercial deferiprone DR tablets discussed above.

In particular, without being bound by theory, the tablet-core of the disclosed pharmaceutical formulations has the advantage of having a composition based on excipients with non-pH-dependent solubility, and therefore, they do not directly interfere with the release of deferiprone at the different pH values within the gastrointestinal tract. This allows for reproducibility of expected and desirable release profiles.

Compositions

In one aspect is provided a modified release tablet comprising: (a) a core comprising deferiprone in an amount of about 85.0% to about 95.0% by weight of the tablet, a modifying release agent comprising a hydroxypropylmethylcellulose polymer having a viscosity of 100 cP and optionally a hydroxypropylmethylcellulose polymer having a viscosity of 4000 cP in an amount of about 4.0% to about 10.0% by weight of the tablet, a lubricant and/or glidant in an amount of about 0.2% to about 2.0% by weight of the tablet, and additional pharmaceutically acceptable excipients in an amount of about 0.0 to 5.0% by weight of the tablet; and (b) an enteric coating; wherein the tablet is suitable for twice a day oral administration.

In another aspect is provided a pharmaceutical formulation in form of modified release enteric coated tablets suitable for twice-a-day oral administration, wherein the pharmaceutical formulation is a tablet, and wherein the core of the tablet comprises deferiprone in an amount of about 85.0 to 95.0%, a hydroproylmethylcellulose polymer Methocel® K100LV alone or in mixture thereof with a hydroproylmethylcellulose polymer Methocel® K4M as a modifying release agent in an amount of about 4.0 and 10.0%, a lubricant and/or glidant in an amount of about 0.2 to 2.0%, and other suitable pharmaceutically acceptable excipients in an amount of about 0 to 5%, wherein all the amounts calculated by weight on the total weight of the formulation.

It has been found an in vitro release similar to the commercial deferiprone DR tablets could be obtained with hydrophilic polymers as modifying release agent.

In particular, the tablet-core of the pharmaceutical dosage form disclosed herein has the advantage of having a composition based on excipients with non-pH-dependent solubility, and hence they are not directly interfering with the release of deferiprone at the different pH values of the gastrointestinal tract.

This illustrates an improvement in terms of reproducibility of the expected release profiles.

A further surprising advantage linked to the use of these polymers will become evident from the following description.

In some aspects, the deferiprone is present in the core in an amount of about 75.0% to about 98.0% by weight of the tablet. In some aspects, the deferiprone is present in the core in an amount of about 75.0% to about 95.0% by weight of the tablet. In some aspects, the deferiprone is present in the core in an amount of about 80.0% to about 95.0% by weight of the tablet. In some aspects, the deferiprone is present in the core in an amount of about 85.0% to about 95.0% by weight of the tablet. In some aspects, the deferiprone is present in the core in an amount of about 85.0%, or about 86.0%, or about 87.0%, or about 88.0%, or about 89.0%, or about 90.0%, or about 91.0%, or about 92.0%, or about 93.0%, or about 94.0%, or about 95.0% by weight of the tablet.

In some aspects, the deferiprone is present in the core in an amount of about 400 mg to about 2000 mg. In some aspects, the deferiprone is present in the core in an amount of about 500 mg to about 1500 mg. In some aspects, the deferiprone is present in the core in an amount of about 600 mg to about 1400 mg. In some aspects, the deferiprone is present in the core in an amount of about 700 mg to about 1300 mg. In some aspects, the deferiprone is present in the core in an amount of about 800 mg to about 1200 mg. In some aspects, the deferiprone is present in the core in an amount of about 900 mg to about 1100 mg. In some aspects, the deferiprone is present in the core in an amount of about 500 mg, or about 600 mg, or about 700 mg, or about 800 mg, or about 900 mg, or about 1000 mg, or about 1100 mg, or about 1200 mg, or about 1300 mg, or about 1400 mg, or about 1500 mg. In some aspects, the deferiprone is present in the core in an amount of about 1000 mg.

A commercial example of a hydroxypropylmethylcellulose polymer (HPMC) having a viscosity of about 100 cP in water is Methocel® K100LV, which is a thickener with low substitution. Its viscosity is determined at 2% addition in water at 20° C.

A commercial example of a hydroxypropylmethylcellulose polymer (HPMC) having a viscosity of about 4000 cP in water is Methocel® K4M, which is a medium molecular weight hydroxypropyl methylcellulose (HPMC) thickener. Also, its viscosity is determined at 2% addition in water at 20° C.

Both are commercially available from DuPont (Delaware, USA) or from Colorcon Inc (California, USA).

In some aspects, the modifying release agent is present in an amount of about 2.0% to about 15.0% by weight of the tablet. In some aspects, the modifying release agent is present in an amount of about 3.0% to about 12.0% by weight of the tablet. In some aspects, the modifying release agent is present in an amount of about 4.0% to about 10.0% by weight of the tablet. In some aspects, the modifying release agent is present in an amount of about 5.0% to about 10.0% by weight of the tablet. In some aspects, the modifying release agent is present in an amount of about 6.0% to about 9.0% by weight of the tablet. In some aspects, the modifying release agent is present in an amount of about 7.0% to about 8.0% by weight of the tablet. In some aspects, the modifying release agent is present in an amount of about 5.0% by weight of the tablet. In some aspects, the modifying release agent is present in an amount of about 6.0% by weight of the tablet. In some aspects, the modifying release agent is present in an amount of about 7.0% by weight of the tablet. In some aspects, the modifying release agent is present in an amount of about 8.0% by weight of the tablet. In some aspects, the modifying release agent is present in an amount of about 9.0% by weight of the tablet. In some aspects, the modifying release agent is present in an amount of about 10.0% by weight of the tablet.

In some aspects, the modifying release agent comprises a hydroxypropylmethylcellulose polymer having a viscosity of 100 cP in an amount of about 7.5% by weight of the tablet.

In some aspects, the modifying release agent comprises a mixture of hydroxypropylmethylcellulose polymer having a viscosity of 100 cP and a hydroxypropylmethylcellulose polymer having a viscosity of 4000 cP. In some aspects, the mixture of hydroxypropylmethylcellulose polymer having a viscosity of 100 cP and the hydroxypropylmethylcellulose polymer having a viscosity of 4000 cP is present in an amount of about 5% by weight of the tablet. In some aspects, the hydroxypropylmethylcellulose polymer having a viscosity of 100 cP is present in an amount of about 1.0% by weight to about 5.0% by weight of the tablet and the hydroxypropylmethylcellulose polymer having a viscosity of 4000 cP is present in an amount of about 1.0% by weight to about 5.0% by weight of the tablet.

In some aspects, the modifying release agent comprises a mixture of hydroxypropylmethylcellulose polymer having a viscosity of 100 cP and a hydroxypropylmethylcellulose polymer having a viscosity of 4000 cP in an amount of about 1.0% by weight of the tablet and about 4.0% by weight of the tablet, respectively. In some aspects, the modifying release agent comprises a mixture of hydroxypropylmethylcellulose polymer having a viscosity of 100 cP and a hydroxypropylmethylcellulose polymer having a viscosity of 4000 cP in an amount of about 2.0% by weight of the tablet and about 3.0% by weight of the tablet, respectively. In some aspects, the modifying release agent comprises a mixture of hydroxypropylmethylcellulose polymer having a viscosity of 100 cP and a hydroxypropylmethylcellulose polymer having a viscosity of 4000 cP in an amount of about 3.0% by weight of the tablet and about 2.0% by weight of the tablet, respectively. In some aspects, the modifying release agent comprises a mixture of hydroxypropylmethylcellulose polymer having a viscosity of 100 cP and a hydroxypropylmethylcellulose polymer having a viscosity of 4000 cP in an amount of about 4.0% by weight of the tablet and about 1.0% by weight of the tablet, respectively.

In some aspects, the ratio between the hydroxypropylmethylcellulose polymer having a viscosity of 100 cP and the hydroxypropylmethylcellulose polymer having a viscosity of 4000 cP is 10:90, or 20:80, or 30:70, or 40:60, or 50:50, or 60:40, or 70:30, or 80:20, or 90:10. In some aspects, the ratio between the hydroxypropylmethylcellulose polymer having a viscosity of 100 cP and the hydroxypropylmethylcellulose polymer having a viscosity of 4000 cP is 40:60.

In some aspects, Methocel® K100LV can be used alone in an amount of 7.5%, while in another aspect, a mixture of Methocel® K100LV and Methocel® K4M can be used in an amount of 5% by weight. In some aspects, the Methocel®

K100LV and Methocel® K4M are in the amount of 2% and 3.0% by weight, respectively (ratio 40:60).

Deferiprone can cause gastric irritation if released in the fasted stomach, and some degradation by acidic hydrolysis is possible. Therefore, in some aspects, the disclosed modified release tablet contains an enteric coating. In some aspects, the enteric coating serves both to delay dissolution of deferiprone and to avoid dissolution in the stomach, in particular the stomach of a fasted patient, as well as in diluents such as water, ethanol, propylene glycol, or mixtures thereof.

Due to the enteric coating, the disclosed modified release tablets have negligible dissolution in the fasted stomach but will more rapidly dissolve in the intestines.

In some aspects, the enteric coating comprises enteric polymers. In some aspects, the enteric polymers for the enteric coating include, e.g., hydroxypropyl methylcellulose acetate succinate (also referred to as hypromellose acetate succinate or HPMCAS), IPMC phthalate (also referred to as hypromellose phthalate), polyvinyl acetate phthalate, cellulose acetate phthalate, cellulose acetate trimellitate, shellac, zein, methacrylic acid copolymers (e.g., methacrylic acid copolymer Type C Dispersion 30%), derivatives thereof, and combinations thereof.

In some aspects, the enteric polymers in the enteric coating are IPMC acetate succinate and methacrylic acid copolymers, e.g., methacrylic acid copolymer type C in aqueous dispersion.

In some aspects, the enteric polymer in the coating is about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, or 4%, by weight of the tablet, or a range between any two of the preceding values, e.g., 0.5-1%, 0.5-2%, 0.5-3%, 0.5-4%, 0.6-1%, 0.6-2%, 0.6-3%, 0.6-4%, 0.7-1%, 0.7-2%, 0.7-3%, 0.7-4%, 1-1.5%, 1.1-1.7%, 1-2%, 1.5-2%, 1-3%, 1-3.5%, or 1-4%, by weight of the tablet. In other aspects, the enteric polymer in the coating is about 2.0% or about 3.0% by weight of the tablet.

In some aspects, the modified release tablets comprise a thicker enteric coating (e.g., 2-3% by weight). In some aspects, the modified release tablets exhibit a release profile similar to the commercial DR deferiprone product, whose enteric coating is about 1.4-1.5% weight of the tablet.

In some aspects, the enteric coating comprises, in addition to the enteric polymer, other excipients, including for example, a plasticizer, a lubricant or anti-tack agent such as talc, an opacifier, a colorant, a diluent, or any combination thereof.

In some aspects, the plasticizer is diethyl phthalate, citrate esters such as triethyl citrate, polyethylene glycol, glycerol, acetylated glycerides, acetylated citrate esters, dibutyl sebecate, castor oil, or any combination thereof.

In some aspects, the enteric coating may further comprise a diluent (e.g., lactose, sucrose, fructose, mannitol, and the like, or combinations thereof). In some aspects, the enteric coating comprises talc as the lubricant or anti-tack agent.

In some aspects, the enteric coating comprises a methacrylic acid copolymer dispersion. In some aspects, the enteric coating comprises an ethacrylic acid—ethyl acrylate copolymer (1:1) dispersion in water and propylene glycol. The ethacrylic acid—ethyl acrylate copolymer (1:1) is available as Eudragit® L30-D55 from Evonik Operations GmbH, Essen Germany.

In some aspects, the enteric coating comprises methacrylic acid-methacrylate copolymer (1:1) in an alcoholic solution. In some aspects, the methacrylic acid—methacrylate copolymer (1:1) is present in a concentration of 5-15% w/w. or 10% w/w, with triethyl citrate as plasticizer. In some aspects, the triethyl citrate is present in a concentration in relation to the polymer of 2-5% w/w, or 3% w/w.

Methacrylic acid—methacrylate copolymer (1:1) is available as Eudragit® L100 (dissolution pH around 6.8) and is commercially available, for example from Sigma-Aldrich (Missouri, USA).

In some aspects, the enteric coating can be applied according to methods known to the skilled person. In some aspects, the enteric coating can be applied over 15 to 20 minutes.

In some aspects, the core may comprise one or more pharmaceutically acceptable excipients such as bulking agents and/or basic excipient.

Advantageously, the buking agent when present can increase tablet hardness. In some aspects, the bulking agent is selected from the group consisting of calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, alpha-lactose monohydrate.

In some aspects, the basic excipient is selected from the group consisting of metal oxides, metal hydroxides, basic salts of weak acids, and a combination thereof. Metal oxides include, but are not limited to, magnesium oxide, aluminum oxide, and zinc oxide. Metal hydroxides include, but are not limited to, sodium hydroxide, potassium hydroxide, magnesium hydroxide, and calcium hydroxide. Basic salts of weak acids include, but are not limited to, sodium or potassium salts of carbonate, bicarbonate, acetate, and citrate. In some aspects, the basic excipient is magnesium oxide, meglumine or a combination thereof. In some aspects, the basic excipient is magnesium oxide.

In some aspects, the modified release tablets comprise a lubricant to prevent sticking to the tooling during compression into tablets, and/or a glidant to improve flow in the tableting process, or combinations thereof.

In some aspects, the lubricant is selected from the group consisting of, but not limited to, magnesium stearate, calcium stearate, stearic acid, sodium stearyl fumarate, or combination thereof. In some aspects, the lubricant is selected is selected from the group consisting of magnesium stearate, calcium stearate, stearic acid, sodium stearyl fumarate, talc, and a combination thereof.

In some aspects, the lubricant is magnesium stearate. In some aspects, the glidant is selected from the group consisting of, but not limited to, colloidal silicon dioxide, starch and talc. In some aspects, the glidant is colloidal silicon dioxide or combination thereof.

In some aspects, the core of modified release tablet comprises a mixture of magnesium stearate and colloidal silicon dioxide.

In some aspects, the lubricant is present in an amount from about 0 to about 5.0% by weight of the tablet. In some aspects, the lubricant is present in an amount from about 0 to about 4.0% by weight of the tablet. In some aspects, the lubricant is present in an amount from about 0 to about 3.0% by weight of the tablet. In some aspects, the lubricant is present in an amount from about 0 to about 2.0% by weight of the tablet. In some aspects, the lubricant is present in an amount of about 0.5% by weight of the tablet. In some aspects, the lubricant is present in an amount of about 1.0% by weight of the tablet. In some aspects, the lubricant is present in an amount of about 1.5% by weight of the tablet. In some aspects, the lubricant is present in an amount of about 2.0% by weight of the tablet. In some aspects, the lubricant is present in an amount of about 2.5% by weight of the tablet. In some aspects, the lubricant is present in an amount of about 3.0% by weight of the tablet.

In some aspects, the core comprises:
i) deferiprone in an amount of 91% by weight of the tablet;
ii) Methocel® K100LV in an amount of 7.5% by weight of the tablet; and
iii) a mixture of a lubricant and glidant in an amount of 1.5% by weight of the tablet.

In some aspects, the core comprises:
i) deferiprone in an amount of 93% by weight of the tablet;
ii) Methocel® K100LV in an amount of 2.0% by weight of the tablet;
iii) Methocel® K4M in an amount of 3.0 by weight of the tablet;
iv) a mixture of a lubricant and glidant in an amount of 2.0% by weight of the tablet.

In some aspects, the modified release tablets are debossed with a score line, to make it easy for the patient to break the tablets into two approximately equal parts to enable administration of half tablets, allowing a dosing flexibility.

When the tablet is broken, its surface at the interface is no longer protected by the enteric coating, and some dissolution in the stomach acid may be observed. But, as long as said dissolution is around 20% at acidic pH, this is not considered a serious issue in terms gastric side effects.

Figure 6:
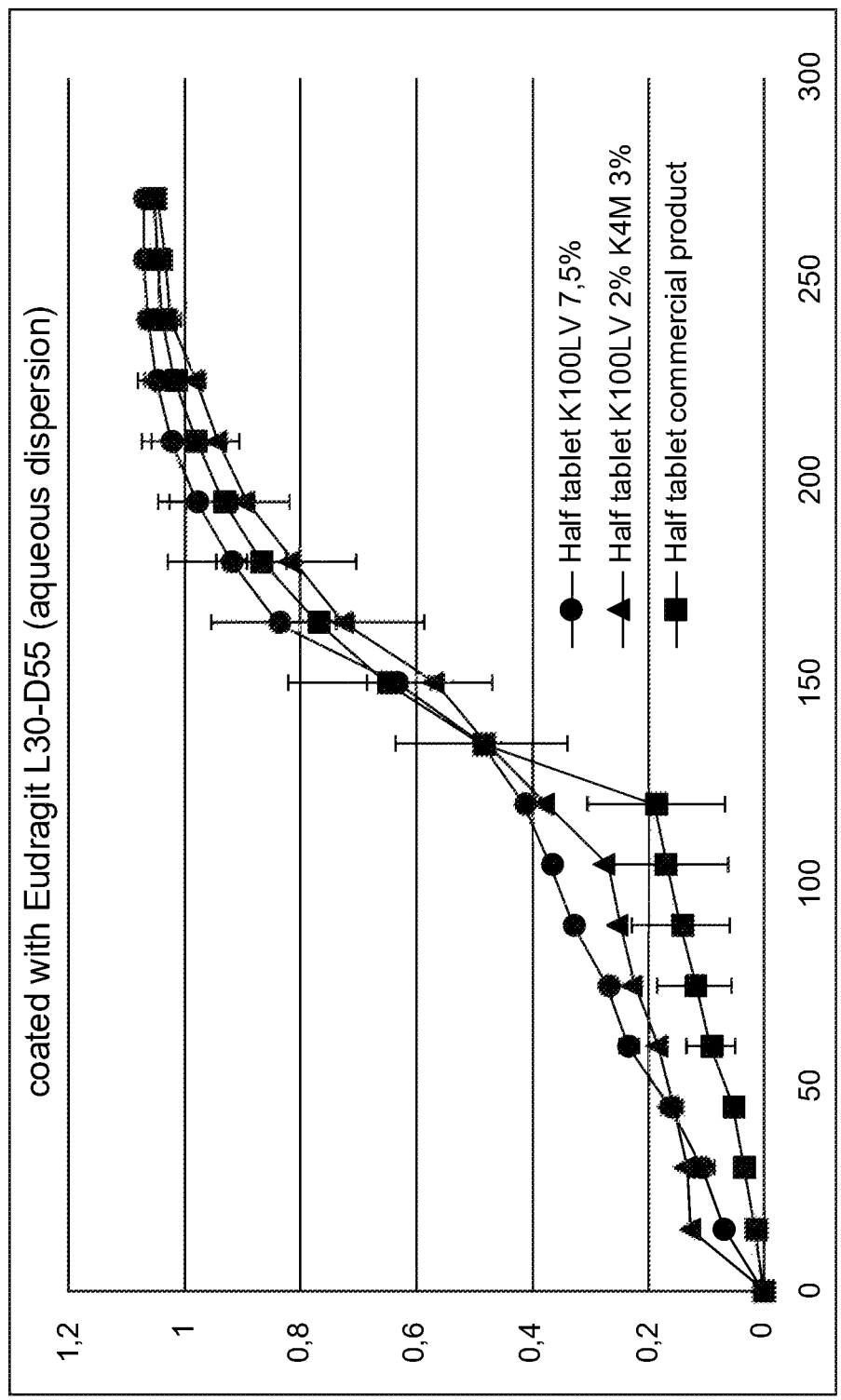
FIG. 6: Dissolution tests of the half-coated tablets in 900 ml of pH 1.2 medium (120 min) and then pH 6.8 medium, basket (apparatus 1) having rotational speed of 100 rpm. The line with a triangular indicator is referred to as the commercial product.

As shown in FIG. 6, although the release of the disclosed modified release tablets is a small amount higher at low pH than the commercial tablets, the half tablets of the disclosed modified release tablets do not show any undesired burst effect when a change of the pH occurs.

In fact, it is well known that transient higher concentrations and hence plasma levels of deferiprone could be associated with transient increase of liver enzymes and other side effects (Cohen E R et al Br J Haematology, 2000, 108, 305-312).

Advantageously, a tablet of the present disclosure embraces the attributes of an enteric coated tablet without its deficiencies, so that tablets can be halved to enable fine tuning of the dosing, and therefore, to administer whole tablets, half tablets, or any combination thereof. Half tablets of the disclosure substantially resist dissolution in acidic media (0.1 N HCl), representing the fasted stomach contents, as do whole tablets. And, at a higher pH representing the contents of the small intestine, the half tablets also exhibit a rate of dissolution similar to whole tablets, but without the undesired burst effect of the reference product on the market.

The release profile of the disclosed modified release tablets has been determined in different dissolution media varying the pH according to the conditions reported in Examples 2 and 3.

In some aspects, the modified release tablets disclosed herein give rise to a dissolution profile at pH 6.8 similar to that of Ferriprox® tablets as approved by FDA and sold in the United States. In some aspects, the modified release tablets show the same bioavailability at the steady state, making it suitable for a twice a day oral administration.

In some aspects, the modified release tablet formulation is bioequivalent in the steady state to the immediate release Ferriprox® tablets for three times a day administration, the mean ratio of AUC (over 24 hours) and the mean ratio of $C_{max}$ for the tablets of the disclosure relative to the immediate release (IR) tablets would be within 80% to 125%.

In some aspects, in the steady state, the disclosed modified release tablets when administered twice-a-day would be able to achieve the same maximum peak concentrations ($C_{max}$) as IR tablets of Ferriprox®, when the IR tablets were given three times a day, and the total amount absorbed (AUC) would be the same for both products over a 24-hour period.

Methods of Preparation

In another aspect is provided a process for the preparation of the modified release tablet as disclosed herein, said process comprising:
i) mixing deferiprone with the modifying release agent and the pharmaceutically acceptable excipients, if present to form a mixture;
ii) wet-granulating the mixture obtained in step (i) in a high shear granulator followed by drying and screening to produce a granulate;
iii) mixing the granulate obtained in step (ii) with the lubricant/glidant to form a mixture;
iv) compressing the mixture obtained in step (iii) to form a tablet;
v) and coating the tablet.

In another aspect is provided a process for the preparation of the modified release tablet as disclosed herein, said process comprising:
i) mixing deferiprone with the modifying release agent and the pharmaceutically acceptable excipients, if present;
ii) adding the lubricant/glidant and further mixing to form a mixture;
iii) directly compressing the mixture obtained in step (ii) to form a tablet; and iv) coating the tablet.

Apparatus and conditions for direct compression and/or compression upon granulation are known to the skilled person in the art.

The modified release tablets could be prepared in any suitable weight. In some aspects, the tablets are prepared in a weight of about 500 mg to about 2500 mg. In some aspects, the tablets are prepared in a weight of about 600 mg to about 2000 mg. In some aspects, the tablets are prepared in a weight of about 800 mg to about 1500 mg. In some aspects, the tablets are prepared in a weight of about 1000 mg to about 1200 mg.

Other pharmaceutically acceptable excipients and procedures mentioned herein can be found in, for example, Handbook of Pharmaceutical Excipients, Third Edition, edited by Arthur H. Kibbe, American Pharmaceutical Association, Washington, USA and Pharmaceutical Press, London; and Lexikon der Hilfsstoffe fi.ir Pharmazie, Kosmetik and angrenzende Gebiete edited by H. P. Fiedler, 4th Edition, Editor Cantar, Aulendorf and earlier editions.

In some aspects, the modified release tablet can be administered to patients using dosing regimens useful for the therapeutic use of the pharmaceutical formulations described herein In some aspects, the oral daily dose with food of deferiprone could range from 75 mg/kg to 100 mg/kg.

In some aspects, the modified release tablet is administered to a subject in need thereof twice daily. In some aspects, the modified release tablet is administered once daily.

In some aspects, the unit dose of deferiprone in the modified release tablets shall be comprised between 500 and 1500 mg, or between 600 and 1000 mg, depending on the frequency of administration.

Methods of Treatment

The claimed formulations are useful for the treatment of diseases which cause an overload of iron, or for the prevention and/or treatment of diseases which are caused by an overload of iron In some aspects, the subject in need thereof suffers from iron overload due to transfusional iron overload, or due diseases such as thalassemia, myelodysplasia, or sickle cell disease.

In some aspects, the subject in need thereof suffers from a neurodegenerative disease (e.g., Parkinson's disease, amyotrophic lateral sclerosis (ALS), Huntington's disease, Friedreich's Ataxia, Pantothenate Kinase Associated Neurodegeneration (PKAN), or neurodegeneration with brain iron accumulation (NBIA).

In some aspects, the subject in need thereof suffers from iron overload that is transfusional iron overload. In certain aspects, the subject suffers from transfusional iron overload and whose prior chelation therapy is inadequate.

In certain aspects, the subject suffers from transfusion iron overload and has a cardiac MRI T2* of 20 ms or less (e.g., 10 ms).

In another aspect is provided the modified release tablet as described herein for use in the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

In another aspect is provided a method of treating a disease which causes an overload of iron, comprising administering the modified release tablet as described herein. In some aspects, the disease is thalassemia or sickle cell anemia. In some aspects, the iron overload is transfusional iron overload.

In another aspect is provided a method of treating and/or preventing a disease which is caused by an overload of iron, comprising administering the modified release tablet as described herein. In some aspects, the iron overload is transfusional iron overload.

In another aspect is provided the modified release tablet as described herein for the manufacture of a medicament for the treatment of diseases which cause an overload of iron, or for the prevention and/or treatment of diseases which are caused by an overload of iron. In some aspects, the disease is thalassemia or sickle cell anemia. In some aspects, the iron overload is transfusional iron overload.

The disclosure is illustrated in detail by the following examples.

EXAMPLES

Example 1—Preparation of the Tablets

Tablets were prepared by direct compression using a rotary tablet press (Officine Meccaniche Ronchi, AM8S) equipped with oblong punches having dimensions of 22 mm×10 mm. Compression force was set at 25 kN in order to have tablets with a crushing strength of about 70 N.

The hydrophilic matrices consisted of mixtures containing 1000 mg of active and different percentages of hypromellose polymer (HPMC) in two viscosity grades (Methocel® K100LV, Methocel® K4M, Colorcon, USA).

TABLE 1

Formulations of oblong tablets formulated with hydrophilic swellable excipient

| MATRIX NAME | API (mg) | Methocel ® K100LV (mg) | Methocel ® K4M (mg) |
|---|---|---|---|
| M K100LV 5% | 1000 | 50 | 1 |
| M K4M 5% | 1000 | / | 50 |
| M K100LV 7.5% | 1000 | 75 | / |
| M K100LV 10% | 1000 | 100 | / |
| M K4M 10% | 1000 | 1 | 100 |
| M K100LV 2% and K4M 3% | 1000 | 20 | 30 |
| M K100LV 3% and K4M 3% | 1000 | 30 | 30 |
| M K1000LV 5% and K4M 2.5% | 1000 | 50 | 25 |
| M K100LV 5% and K4M 3.25% | 1000 | 50 | 32.5 |
| M K100LV 5% and K4M 4% | 1000 | 50 | 40 |

Example 2—Dissolution Test

The spectrum of maximum absorption of the active was acquired in the various fluids in which the release tests will be conducted by means of a spectrophotometer.

Compositions of dissolution media are reported below.

pH 1.2: for 1 L, 3.73 g KCl, 7.07 ml HCl 1 N (deionized water up to volume);

pH 4.5: for 1 L, 6.80 g of $KH_2PO_4$ (deionized water up to volume);

pH 6.8: for 1 L, 6.80 g $KH_2PO_4$, 0.90 g of NaOH {deionized water up to volume).

Calibration curves were built for each of the release media both at the wavelength of 276 nm at which a peak of absorbance was recorded, and at 243 nm, in which reduced absorption was observed, in order not to exceed the instrument maximum absorbance value.

The release test of the commercial product was analyzed at the wavelength of 276 nm both in pH 4.5 phosphate, and with the pH change mode (HCl 0.1 N for the first 120 minutes and phosphate buffer pH 6.8 for the remainder of the test). At high values of absorbance (over 30% of the release) sampling, dilutions and manual readings was performed.

Release tests were carried out in a dissolution test paddle apparatus (USP type 2) with a rotation speed of 50 rpm and basket apparatus (USP type 1) with a rotation speed of 100 rpm. The tests were always conducted in 900 mL of dissolution medium at 37° C. For the experimental formulations, the active ingredient was quantified by spectrophotometry at a wavelength of 243 nm.

Figure 2:
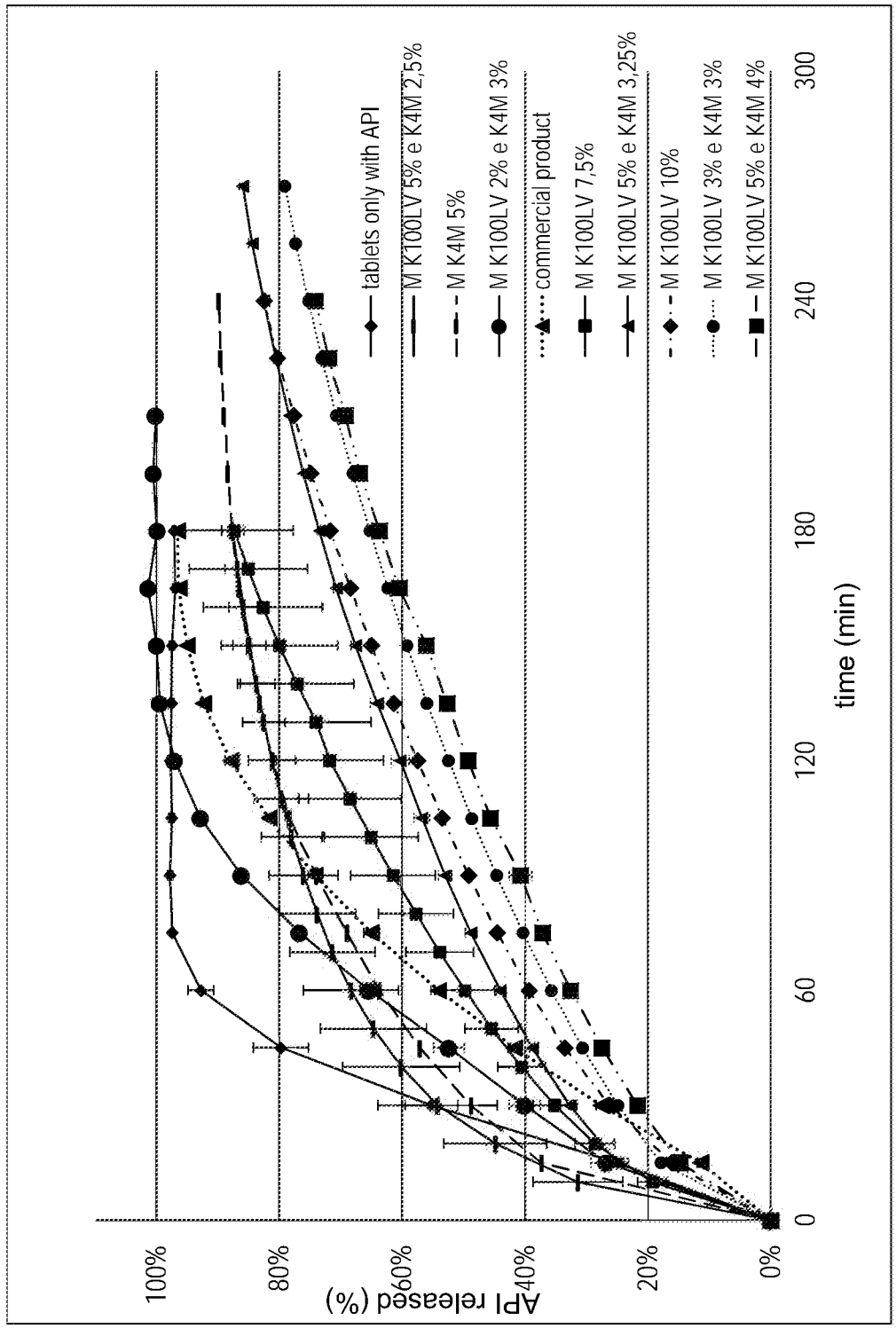
FIG. 2: Dissolution tests of HPMC formulations carried out in 900 ml of pH 4.5 medium, paddle (apparatus 2) having rotational speed of 50 rpm. The line with a triangular indicator is referred to as the commercial product.

The results for the uncoated tablets at pH 6.8 and 4.5 are reported in FIGS. 1 and 2.

It can be appreciated that, the tablets comprising Methocel® K100LV 7.5% or a mixture of Methocel® K100LV 2% and K4M 3% exhibit the release profile more similar to the reference product.

Example 3—Gastroresistant Coating

Starting from the results of the non-coated tablets, those formulated with
  Methocel® K100LV 7.5%
  Methocel® K100LV 2% and K4M 3%
were selected to be coated with a gastroresistant film.

Tablets were then coated with a different acrylic polymer having a dissolution pH around 6 and formulated in aqueous dispersion:

Eudragit® L30-D55 aqueous dispersion 60% w/w (containing 25% solids)
Deionized water 38% w/w
Propylene glycol 2% w/w
Process parameters were the followings:
Nozzle: 0.8 mm
Atomization pressure: 0.8 bar
Control pressure: 2 bar
Pattern pressure: 0.5 bar
Peristaltic pump: 2 rpm
Air temperature: 57° C.

Coating process lasted for 20 minutes and samples were collected every 5 minutes in order to test different coating amounts by dissolution test. The analysis has been carried out in the same conditions of the previous ones.

Figure 3:
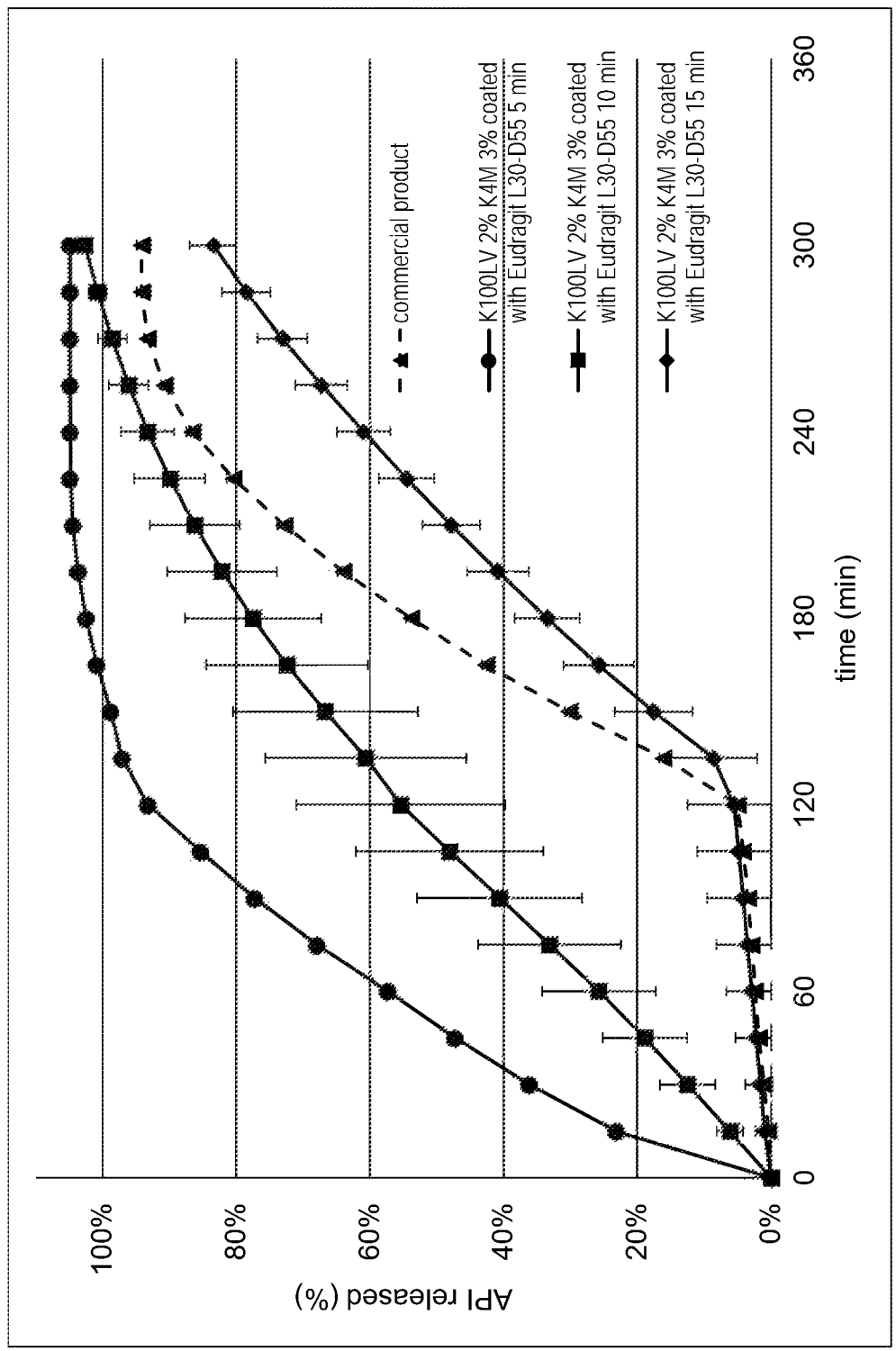
FIG. 3: Dissolution tests of HPMC formulations carried out in 900 ml of pH 1.2 medium (120 min) and then pH 6.8 medium, basket (apparatus 1) having rotational speed of 100 rpm. The line with a triangular indicator is referred to as the commercial product.
Figure 4:
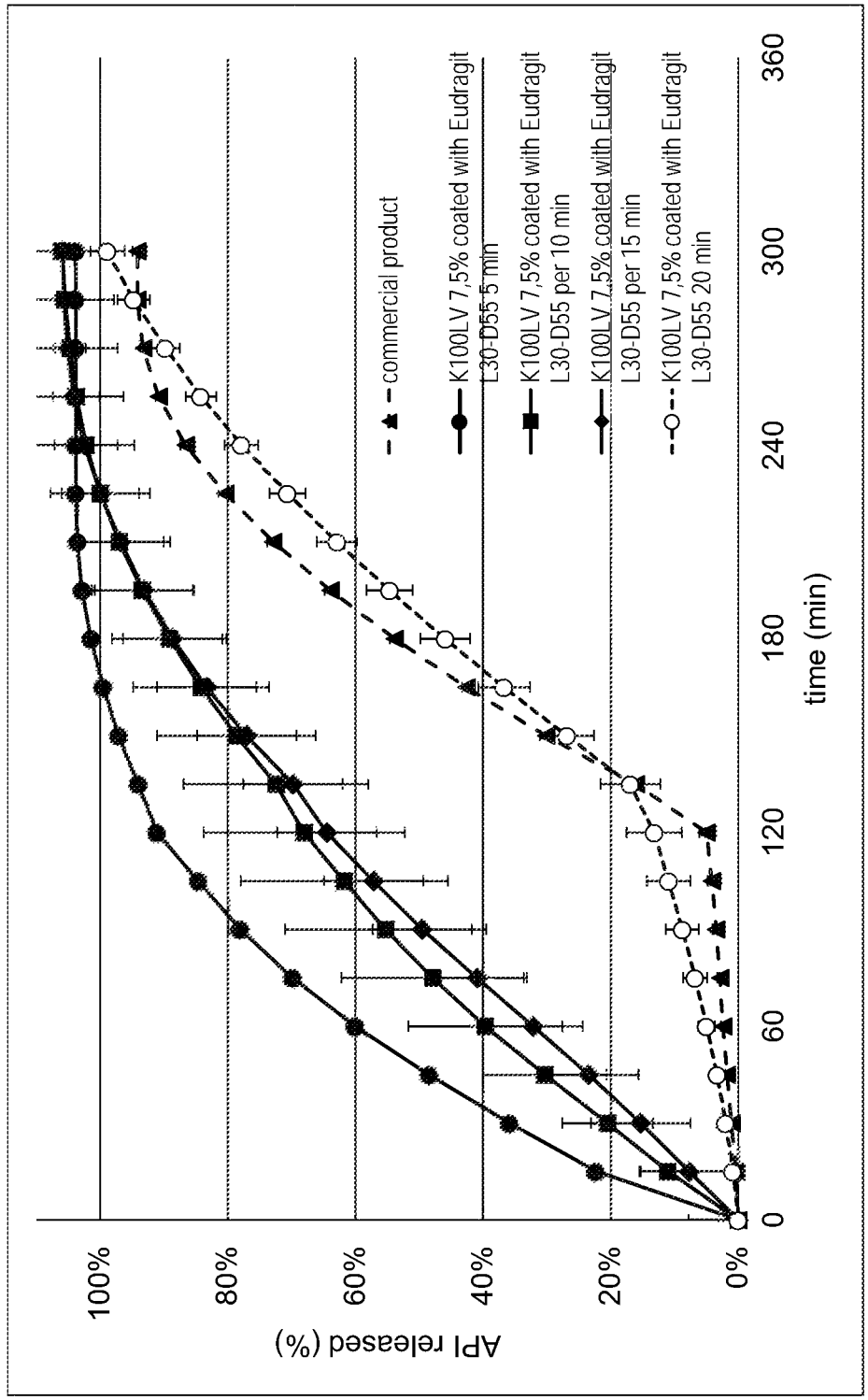
FIG. 4: Dissolution tests of HPMC formulations carried out in 900 ml of pH 1.2 medium (120 min) and then pH 6.8 medium, basket (apparatus 1) having rotational speed of 100 rpm. The line with a triangular indicator is referred to as the commercial product.

The results are reported in FIGS. 3 and 4

K100LV 7.5% tablets had more difficulties in getting coated in the first minutes, for this formulation, in fact, the coating process lasted 5 minutes more than for the K100LV 2% K4M 3% tablets; both reached a 2% weight at the end.

As an alternative method of coating, Eudragit® L100 (dissolution pH around 6.8) in an alcoholic solution (10% w/w) with triethyl citrate (3% w/w in relation with the polymer) was applied.

The coating process has been conducted in a small coating pan (opening diameter 10 cm) and with the following process parameters:
Nozzle: 0.8 mm
Atomization pressure: 0.5 bar
Control pressure: 0.6 bar
Pattern pressure: 2 bar
Peristaltic pump: 2 rpm
Air temperature: 50° C.

The process has been stopped when the tablets reached a weight gain (wg) of 3%.

Dissolution tests have been conducted at 37° in Apparatus 1 (basket) with a rotational speed of 100 rpm in the following dissolution media:
pH 1.2 (for 1 L, 3.73 g KCl, 7.07 mL HCl 1N and deionized water up to volume) for the first 120 minutes
pH 6.8 (for 1 L, 6.80 g $KH_2PO_4$, 0.90 g of NaOH and deionized water up to volume) for the rest of the dissolution time.

Figure 5:
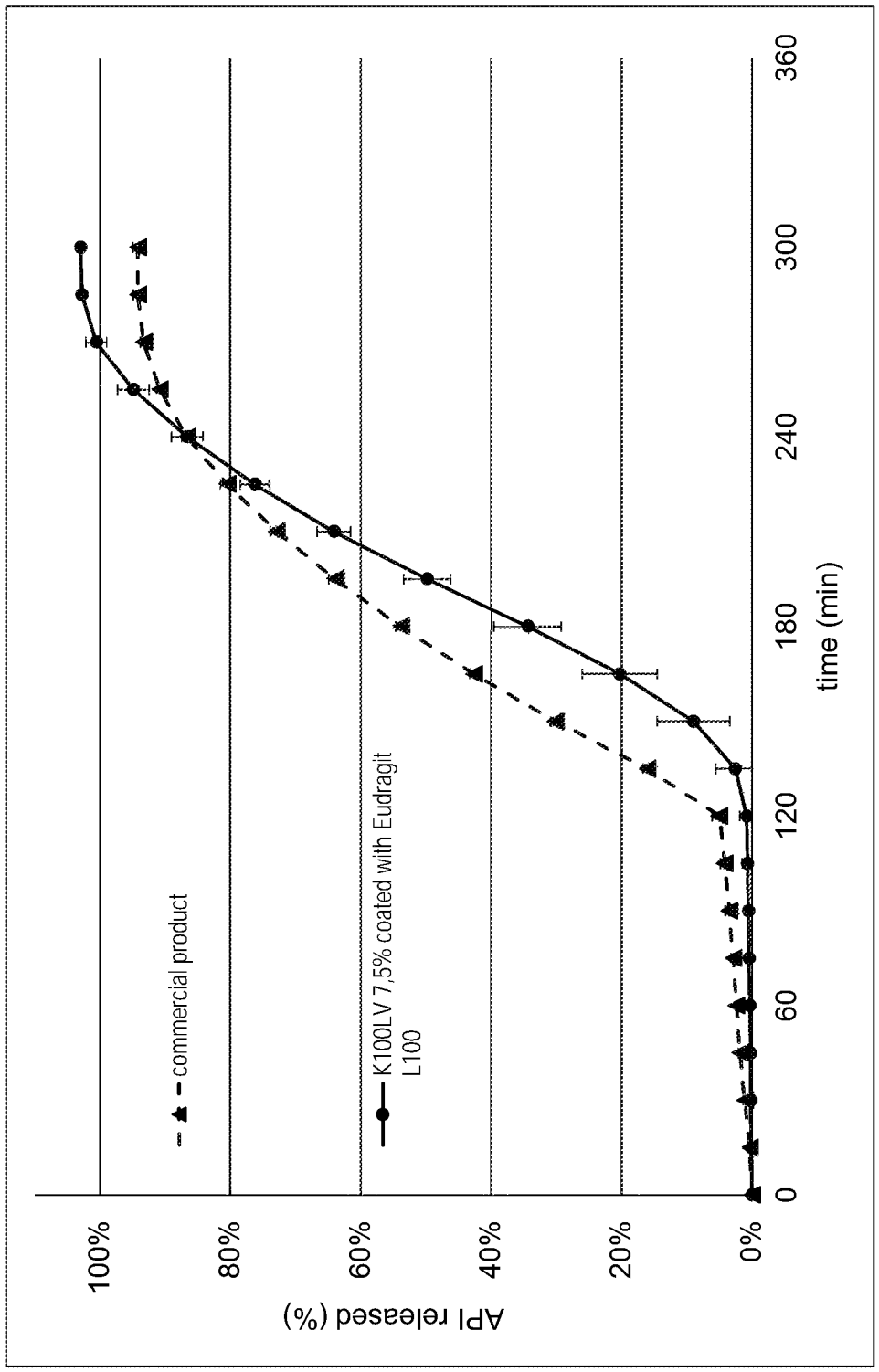
FIG. 5: Dissolution tests of HPMC formulations carried out in 900 ml of pH 1.2 medium (120 min) and then pH 6.8 medium, basket (apparatus 1) having rotational speed of 100 rpm. The line with a triangular indicator is referred to as the commercial product.

The results are reported in FIG. 5.

It can be appreciated, that a release very similar to the reference product was obtained for the K100LV 7.5% tablets.

The release profile of the half tablets according to the disclosure, coated with Eudragit® L30-D55 was also investigated versus half tablets of the reference product.

Dissolution tests have been conducted at 37° C. in Apparatus 1 (basket) with a rotational speed of 100 rpm in the following dissolution media:
pH 1.2 (for 1 L, 3.73 g KCl, 7.07 mL HCl 1N and deionized water up to volume) for the first 120 minutes
pH 6.8 (for 1 L, 6.80 g $KH_2PO_4$, 0.90 g of NaOH and deionized water up to volume) for the rest of the dissolution time.

The results are reported in FIG. 6.

As it can be appreciated, although the release is a little bit higher at low pH than the commercial tablets was observed, the half tablets of the disclosure, when a change of the pH occurs, do not show any undesired burst effect.

In addition to the various aspects described herein, the present disclosure includes the following aspects numbered A1 through A20. This list of aspects is presented as an exemplary list and the application is not limited to these aspects.

A1. A modified release tablet comprising: (a) a core comprising deferiprone in an amount of about 85.0% to about 95.0% by weight of the tablet, a modifying release agent comprising a hydroxypropylmethylcellulose polymer having a viscosity of 100 cP and optionally a hydroxypropylmethylcellulose polymer having a viscosity of 4000 cP in an amount of about 5.0% to about 10.0% by weight of the tablet, a lubricant and/or glidant in an amount of about 0.2% to about 2.0% by weight of the tablet, and additional pharmaceutically acceptable excipients in an amount of about 0.0 to 5.0% by weight of the tablet; and (b) an enteric coating; wherein the tablet is suitable for twice a day oral administration.

A2. The modified release tablet according to A1, wherein the modifying release agent comprises a hydroxypropylmethylcellulose polymer having a viscosity of 100 cP in an amount of about 7.5% by weight.

A3. The modified release tablet according to A1, wherein the modifying release agent comprises a mixture of hydroxypropylmethylcellulose polymer having a viscosity of 100 cP and a hydroxypropylmethylcellulose polymer having a viscosity of 4000 cP in an amount of about 5% by weight.

A4. The modified release tablet according to A3, wherein the ratio between the hydroxypropylmethylcellulose polymer having a viscosity of 100 cP and the hydroxypropylmethylcellulose polymer having a viscosity of 4000 cP is 40:60.

A5. The modified release tablet according to any one of the preceding aspects, wherein the lubricant is selected is selected from the group consisting of magnesium stearate, calcium stearate, stearic acid, sodium stearyl fumarate, talc, and combinations thereof.

A6. The modified release tablet according to A5, wherein the lubricant is magnesium stearate.

A7. The modified release tablet according to any one of the preceding aspects, wherein the glidant is selected from the group consisting of colloidal silicon dioxide, starch, talc, and combinations thereof.

A8. The modified release tablet according to A7, wherein the glidant is colloidal silicon dioxide.

A9. The modified release tablet according to any one of the preceding aspects, wherein the other suitable pharmaceutically acceptable excipients are selected from pH adjusting agents and bulking agents.

A10. The modified release tablet according to any one of the preceding aspects, wherein the enteric coating comprises an enteric polymer, a diluent, and optionally a plasticizer.

A11. The modified release tablet according to A10, wherein the enteric coating comprises an ethacrylic acid—ethyl acrylate copolymer (1:1) dispersion in water and propylene glycol.

A12. The modified release tablet according to A10, wherein the enteric coating comprises methacrylic acid—methacrylate copolymer (1:1) in an alcoholic solution with triethyl citrate.

A13. The modified release tablet according to any one of the preceding aspects, wherein the core of the tablet comprises from 500 to 1500 mg of deferiprone.

A14. The modified release tablet according to claim A13, wherein the core of the tablet comprises 1000 mg of deferiprone.

A15. A process for the preparation of the modified release tablet according to any one of A1 to A14, said process comprising:
  i) mixing deferiprone with the modifying release agent and the other pharmaceutically acceptable excipients, if present to form a mixture;
  ii) wet-granulating the mixture obtained in step (i) in a high shear granulator followed by drying and screening to produce a granulate;
  iii) mixing the granulate obtained in step (ii) with the lubricant/glidant to form a mixture;
  iv) compressing the mixture obtained in step (iii) to form a tablet; and
  v) coating the tablet.

A16. A process for the preparation of the modified release tablet according to any one of A1 to A14, said process comprising:
  i) mixing deferiprone with the modifying release agent and the other pharmaceutically acceptable excipients, if present;
  ii) adding the lubricant/glidant and further mixing to form a mixture;
  iii) directly compressing the mixture obtained in step (ii) to form a tablet; and
  iv) coating the tablet.

A17. A method of treating a disease which causes an overload of iron, comprising administering the modified release tablet of any one of A1 to A14.

A18. A method of treating and/or preventing a disease which is caused by an overload of iron, comprising administering the modified release tablet of any one of A1 to A14.

A19. The method of A17, wherein the disease is thalassemia or sickle cell anemia.

A20. The method of A17, wherein the iron overload is transfusional iron overload.

The invention claimed is:

1. A delayed release tablet comprising: (a) a core comprising about 1000 mg deferiprone, wherein the deferiprone is in an amount of about 85.0% to about 95.0% by weight of the tablet, a modifying release agent comprising a hydroxypropylmethylcellulose polymer having a viscosity of 100 cP and optionally a hydroxypropylmethylcellulose polymer having a viscosity of 4000 cP in an amount of about 5.0% to about 10.0% by weight of the tablet, a lubricant and/or glidant in an amount of about 0.2% to about 2.0% by weight of the tablet, and additional pharmaceutically acceptable excipients in an amount of about 0.0 to 5.0% by weight of the tablet; and (b) an enteric coating; wherein the tablet is suitable for twice a day oral administration; and wherein the tablet releases less than about 20% of the deferiprone within 120 minutes when measured by USP Apparatus Type I basket method at 100 rpm in 900 mL at 37° C. and a pH of 1.2 and about 60% or more of the deferiprone within 180 minutes when measured by USP Apparatus Type I basket method at 100 rpm in 900 mL at 37° C. and a pH of 6.8.

2. The delayed release tablet according to claim 1, wherein the modifying release agent comprises a hydroxypropylmethylcellulose polymer having a viscosity of 100 cP in an amount of about 7.5% by weight.

3. The delayed release tablet according to claim 1, wherein the modifying release agent comprises a mixture of hydroxypropylmethylcellulose polymer having a viscosity of 100 cP and a hydroxypropylmethylcellulose polymer having a viscosity of 4000 cP in an amount of about 5% by weight.

4. The delayed release tablet according to claim 3, wherein the ratio between the hydroxypropylmethylcellulose polymer having a viscosity of 100 cP and the hydroxypropylmethylcellulose polymer having a viscosity of 4000 cP is 40:60 by weight.

5. The delayed release tablet according to claim 1, wherein the lubricant is selected from the group consisting of magnesium stearate, calcium stearate, stearic acid, sodium stearyl fumarate, talc, and combinations thereof.

6. The delayed release tablet according to claim 5, wherein the lubricant is magnesium stearate.

7. The delayed release tablet according to claim 1, wherein the glidant is selected from the group consisting of colloidal silicon dioxide, starch, talc, and combinations thereof.

8. The delayed release tablet according to claim 7, wherein the glidant is colloidal silicon dioxide.

9. The delayed release tablet according to claim 1, wherein the additional pharmaceutically acceptable excipients are selected from pH adjusting agents and bulking agents.

10. The delayed release tablet according to claim 1, wherein the enteric coating comprises an enteric polymer, a diluent, and optionally a plasticizer.

11. The delayed release tablet according to claim 10, wherein the enteric coating comprises an ethacrylic acid—ethyl acrylate copolymer (1:1) dispersion in water and propylene glycol.

12. The delayed release tablet according to claim 10, wherein the enteric coating comprises methacrylic acid—methacrylate copolymer (1:1) in an alcoholic solution with triethyl citrate.

13. A process for the preparation of the delayed release tablet according to claim 1, said process comprising:
  i) mixing deferiprone with the modifying release agent and the additional pharmaceutically acceptable excipients, if present to form a mixture;
  ii) wet-granulating the mixture obtained in step (i) in a high shear granulator followed by drying and screening to produce a granulate;
  iii) mixing the granulate obtained in step (ii) with the lubricant and/or glidant to form a mixture;
  iv) compressing the mixture obtained in step (iii) to form a tablet; and
  v) coating the tablet.

14. A process for the preparation of the delayed release tablet according to claim 1, said process comprising:
  i) mixing deferiprone with the modifying release agent and the additional pharmaceutically acceptable excipients, if present;
  ii) adding the lubricant and/or glidant and further mixing to form a mixture;
  iii) directly compressing the mixture obtained in step (ii) to form a tablet; and
  iv) coating the tablet.

15. A method of treating a disease which causes an overload of iron, comprising administering the delayed release tablet of claim 1.

16. The method of claim 15, wherein the disease is thalassemia or sickle cell anemia.

17. The method of claim 15, wherein the iron overload is transfusional iron overload.

18. A method of treating and/or preventing a disease which is caused by an overload of iron, comprising administering the delayed release tablet of claim 1.

* * * * *